(12) United States Patent
Phillips

(10) Patent No.: US 9,179,900 B2
(45) Date of Patent: Nov. 10, 2015

(54) HEMOSTATIC DEVICE AND ITS METHODS OF USE

(75) Inventor: Victor Matthew Phillips, Jefferson City, MO (US)

(73) Assignee: Phillips Medical LLC, Jefferson City, MO (US)

(*) Notice: Subject to any disclaimer, the term of this patent is extended or adjusted under 35 U.S.C. 154(b) by 663 days.

(21) Appl. No.: 12/762,886

(22) Filed: Apr. 19, 2010

(65) Prior Publication Data

US 2011/0137338 A1    Jun. 9, 2011

Related U.S. Application Data

(60) Provisional application No. 61/267,685, filed on Dec. 8, 2009.

(51) Int. Cl.
| | |
|---|---|
| *A61B 17/08* | (2006.01) |
| *A61D 1/00* | (2006.01) |
| *A61B 17/00* | (2006.01) |
| *A61M 25/06* | (2006.01) |
| *A61M 29/02* | (2006.01) |

(52) U.S. Cl.
CPC ... *A61B 17/0057* (2013.01); *A61B 2017/00672* (2013.01); *A61M 25/065* (2013.01); *A61M 25/0693* (2013.01); *A61M 29/02* (2013.01)

(58) Field of Classification Search
CPC .............. A61B 17/0057; A61B 2017/00672; A61B 2017/00637; A61B 2019/462; A61B 17/3498; A61B 2017/00654; A61M 25/0693
USPC .............. 606/213, 214; 604/93.01, 103.01, 604/168.01
See application file for complete search history.

(56) References Cited

U.S. PATENT DOCUMENTS

| | | |
|---|---|---|
| 4,738,658 A | 4/1988 | Magro et al. |
| 4,850,960 A | 7/1989 | Grayzel |
| 4,890,612 A | 1/1990 | Kensey |
| 4,895,564 A | 1/1990 | Farrell |
| 4,929,246 A | 5/1990 | Sinofsky |
| 5,061,274 A | 10/1991 | Kensey |
| 5,108,421 A | 4/1992 | Fowler |
| 5,222,974 A | 6/1993 | Kensey et al. |
| 5,282,827 A | 2/1994 | Kensey et al. |
| 5,290,310 A | 3/1994 | Makower et al. |
| 5,306,254 A | 4/1994 | Nash et al. |
| 5,326,350 A | 7/1994 | Li |
| RE34,866 E | 2/1995 | Kensey et al. |
| 5,391,183 A | 2/1995 | Janzen et al. |

(Continued)

OTHER PUBLICATIONS

Merriam-Webster dictionary definition of 'valve'.*

(Continued)

*Primary Examiner* — Katherine M Shi
(74) *Attorney, Agent, or Firm* — Armstrong Teasdale LLP

(57) ABSTRACT

A hemostatic device is provided for sealing a puncture of a vessel. The hemostatic device includes a locator device and an injection tube coupled to the locator device. The locator device includes a device valve that is actuatable to selectively restrict access to a portion of the locator device. The hemostatic device is advanced into the vessel until a first fluid is channeled through the locator device. The device valve is actuated to selectively restrict the first fluid from being channeled through the locator device. A second fluid is injected through the injection tube to facilitate sealing a puncture of the vessel. The hemostatic device is withdrawn from the vessel.

18 Claims, 4 Drawing Sheets

(56) References Cited

U.S. PATENT DOCUMENTS

| | | | |
|---|---|---|---|
| 5,415,657 A | 5/1995 | Taymor-Luria | |
| 5,431,639 A | 7/1995 | Shaw | |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,591,204 A | 1/1997 | Janzen et al. | |
| 5,645,566 A | 7/1997 | Brenneman et al. | |
| 5,653,730 A | 8/1997 | Hammerslag | |
| 5,665,107 A | 9/1997 | Hammerslag | |
| 5,676,689 A | 10/1997 | Kensey et al. | |
| 5,707,393 A | 1/1998 | Kensey et al. | |
| 5,716,375 A | 2/1998 | Fowler | |
| 5,725,498 A | 3/1998 | Janzen et al. | |
| 5,741,223 A | 4/1998 | Janzen et al. | |
| 5,766,157 A | 6/1998 | Tilton, Jr. | |
| 5,766,206 A | 6/1998 | Wijkamp et al. | |
| 5,782,861 A | 7/1998 | Cragg et al. | |
| 5,843,124 A * | 12/1998 | Hammerslag | 606/214 |
| 5,868,762 A | 2/1999 | Cragg et al. | |
| 5,935,147 A | 8/1999 | Kensey et al. | |
| 5,951,583 A | 9/1999 | Jensen et al. | |
| 5,984,950 A | 11/1999 | Cragg et al. | |
| 6,045,570 A | 4/2000 | Epstein et al. | |
| 6,056,768 A | 5/2000 | Cates et al. | |
| 6,090,130 A | 7/2000 | Nash et al. | |
| 6,296,657 B1 | 10/2001 | Brucker | |
| 6,302,898 B1 | 10/2001 | Edwards et al. | |
| 6,315,753 B1 | 11/2001 | Cragg et al. | |
| 6,325,789 B1 | 12/2001 | Janzen et al. | |
| 6,350,274 B1 * | 2/2002 | Li | 606/213 |
| 6,371,974 B1 | 4/2002 | Brenneman et al. | |
| 6,371,975 B2 | 4/2002 | Cruise et al. | |
| 6,500,152 B1 | 12/2002 | Illi | |
| 6,527,734 B2 | 3/2003 | Cragg et al. | |
| 6,544,236 B1 | 4/2003 | Cragg et al. | |
| 6,547,806 B1 | 4/2003 | Ding | |
| 6,610,026 B2 | 8/2003 | Cragg et al. | |
| 6,743,248 B2 | 6/2004 | Edwards et al. | |
| 6,830,756 B2 | 12/2004 | Hnojewyj | |
| 6,863,680 B2 | 3/2005 | Ashby | |
| 6,984,219 B2 | 1/2006 | Ashby et al. | |
| 7,029,489 B1 | 4/2006 | Ashby et al. | |
| 7,037,322 B1 | 5/2006 | Sing et al. | |
| 7,048,710 B1 | 5/2006 | Cragg et al. | |
| 7,144,411 B2 * | 12/2006 | Ginn et al. | 606/213 |
| 7,201,725 B1 | 4/2007 | Cragg et al. | |
| 7,318,933 B2 | 1/2008 | Hnojewyj | |
| 7,335,219 B1 | 2/2008 | Ashby et al. | |
| 7,455,680 B1 | 11/2008 | Ashby et al. | |
| 7,611,479 B2 | 11/2009 | Cragg et al. | |
| 7,625,352 B1 | 12/2009 | Ashby et al. | |
| 2001/0018598 A1 | 8/2001 | Cruise et al. | |
| 2002/0062104 A1 * | 5/2002 | Ashby et al. | 604/93.01 |
| 2003/0088271 A1 | 5/2003 | Cragg et al. | |
| 2003/0100921 A1 | 5/2003 | Addis et al. | |
| 2004/0019328 A1 | 1/2004 | Sing et al. | |
| 2004/0098024 A1 | 5/2004 | Dieck et al. | |
| 2004/0102730 A1 | 5/2004 | Davis et al. | |
| 2004/0176801 A1 | 9/2004 | Edwards et al. | |
| 2005/0085854 A1 * | 4/2005 | Ginn | 606/213 |
| 2006/0100664 A1 | 5/2006 | Pai et al. | |
| 2007/0038245 A1 | 2/2007 | Morris et al. | |
| 2007/0123816 A1 | 5/2007 | Zhu et al. | |
| 2008/0038313 A1 | 2/2008 | Addis et al. | |
| 2008/0046005 A1 | 2/2008 | Lenker et al. | |
| 2008/0071310 A1 | 3/2008 | Hoffman et al. | |
| 2008/0082122 A1 | 4/2008 | Khosravi et al. | |
| 2008/0161849 A1 | 7/2008 | Cates et al. | |
| 2009/0088793 A1 | 4/2009 | Bagaoisan et al. | |
| 2009/0143808 A1 | 6/2009 | Houser | |
| 2009/0171282 A1 | 7/2009 | Pipenhagen et al. | |
| 2010/0312273 A1 | 12/2010 | Kim | |
| 2011/0137338 A1 | 6/2011 | Phillips | |

OTHER PUBLICATIONS

International Search Report and Written Opinion of PCT/US2011/032490; Jun. 29, 2011; 10 pages.

Extended European Search Report of Application No. 11772458.3; Sep. 15, 2014; 7 pages.

A Patent Examination Report No. 1, dated May 20, 2015, from the Australian patent office, for co-pending Australian patent application No. 2011243001 (4 pgs.).

A Communication from the European Patent Office, dated Jul. 22, 2015, for co-pending European patent application No. 11772458.3 (6 pgs).

* cited by examiner

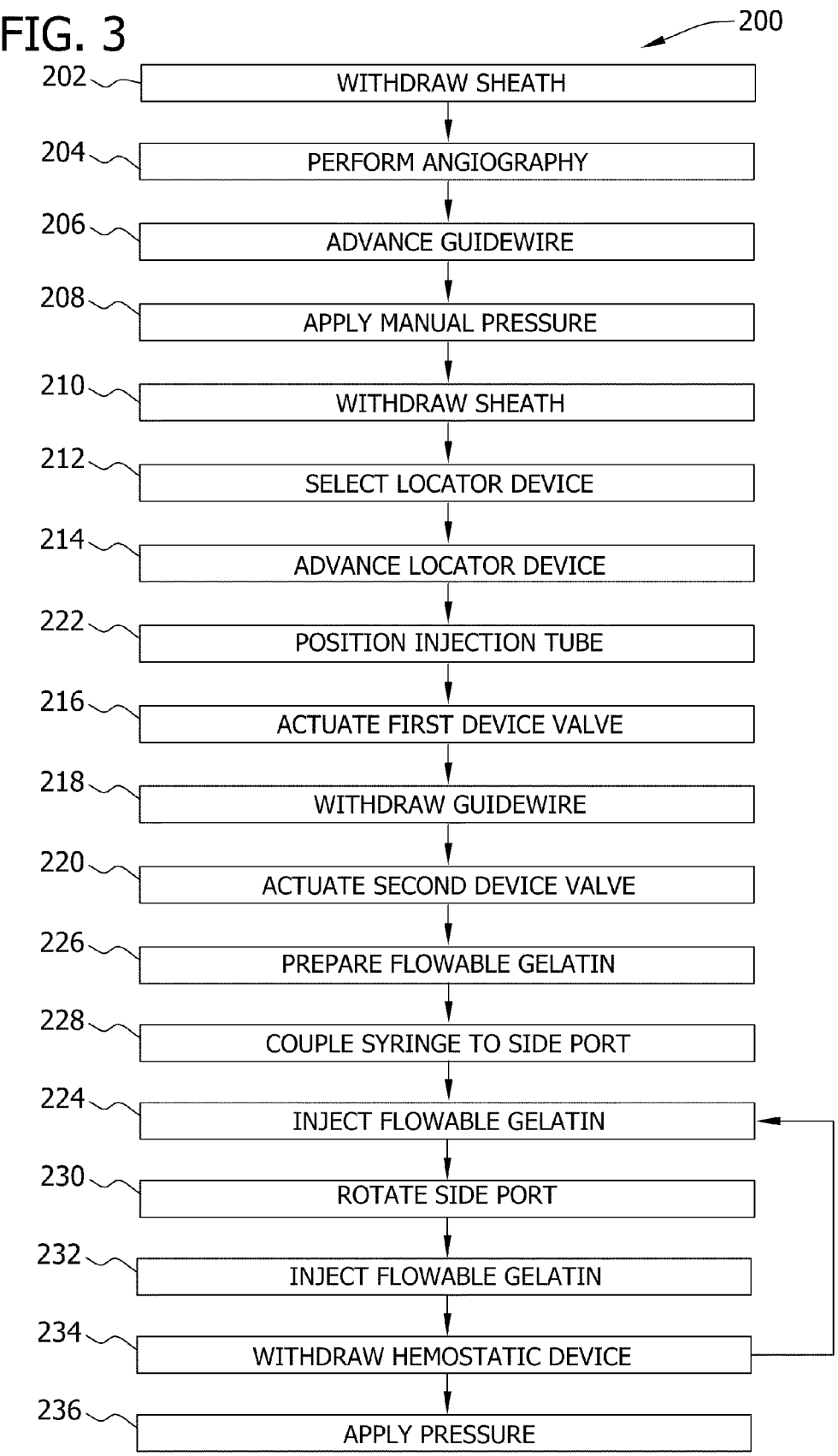

HEMOSTATIC DEVICE AND ITS METHODS OF USE

CROSS REFERENCE TO RELATED APPLICATIONS

This application claims the benefit of U.S. Provisional Application No. 61/267,685, filed Dec. 8, 2009, which is hereby incorporated by reference in its entirety.

BACKGROUND OF THE INVENTION

The subject matter described herein relates generally to medical devices and, more particularly, to a hemostatic device.

Catheter introducers are known to provide an access site to an artery for at least some medical procedures such as cardiac catheterizations or peripheral endovascular procedures. After such medical procedures are conducted, the catheter introducer is removed from the access site, leaving an arterial opening. Generally, excess blood loss endangers and/or traumatizes the patient. One known method of controlling blood loss is through direct manual pressure over the access site.

BRIEF SUMMARY OF THE INVENTION

In one aspect, a method is provided for using a hemostatic device for sealing a puncture of a vessel. The hemostatic device includes a locator device coupled to an injection tube. The locator device includes a device valve that is actuatable to selectively restrict access to a portion of the locator device. The method includes advancing the hemostatic device into the vessel until a first fluid is channeled through the locator device. The device valve is actuated to selectively restrict the first fluid from being channeled through the locator device. A second fluid is injected through the injection tube to facilitate sealing a puncture of the vessel. The hemostatic device is withdrawn from the vessel.

In another aspect, a hemostatic device is provided for sealing a puncture of a vessel. The hemostatic device includes a locator device and an injection tube coupled to the locator device. The locator device includes a device valve that is actuatable to selectively restrict access to a portion of the locator device. The locator device is configured to channel a first fluid therethrough. The injection tube is configured to channel a second fluid therethrough.

In yet another aspect, a hemostatic device is provided for sealing a puncture of a vessel. The hemostatic device includes a locator device and an injection tube coupled to the locator device. The locator device includes a device sidewall and a device valve. The device sidewall defines a device lumen that is configured to channel a first fluid therethrough. The device valve is actuatable to selectively restrict access to the device lumen. The injection tube includes a tube sidewall that defines a tube lumen configured to channel a second fluid therethrough.

BRIEF DESCRIPTION OF THE DRAWINGS

FIG. 3 is a flow chart illustrating an exemplary method using the hemostatic device shown in FIG. 1.

DETAILED DESCRIPTION OF THE INVENTION

The methods and apparatus described herein relate to medical devices and, more particularly, to a hemostatic device. The hemostatic device described herein facilitates sealing a puncture of a vessel. More particularly, the hemostatic device enables positioning an injection tube adjacent to the vessel to inject a gelatin through the injection tube. As such, the hemostatic device facilitates reducing a time required for hemostasis and ambulation.

Figure 1:
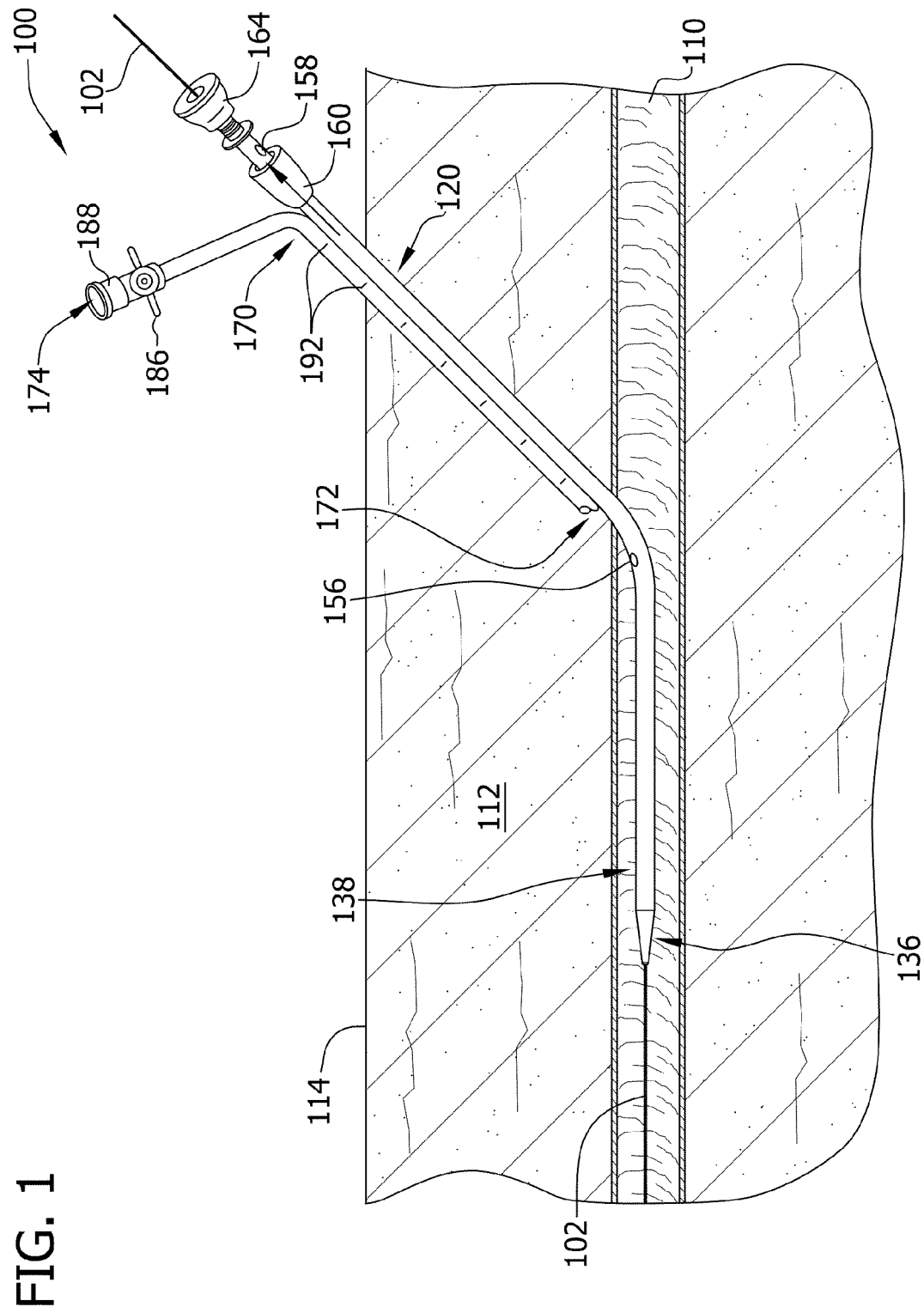
FIG. 1 is a partial cross-sectional view of an access site including an exemplary hemostatic device.
Figure 2:
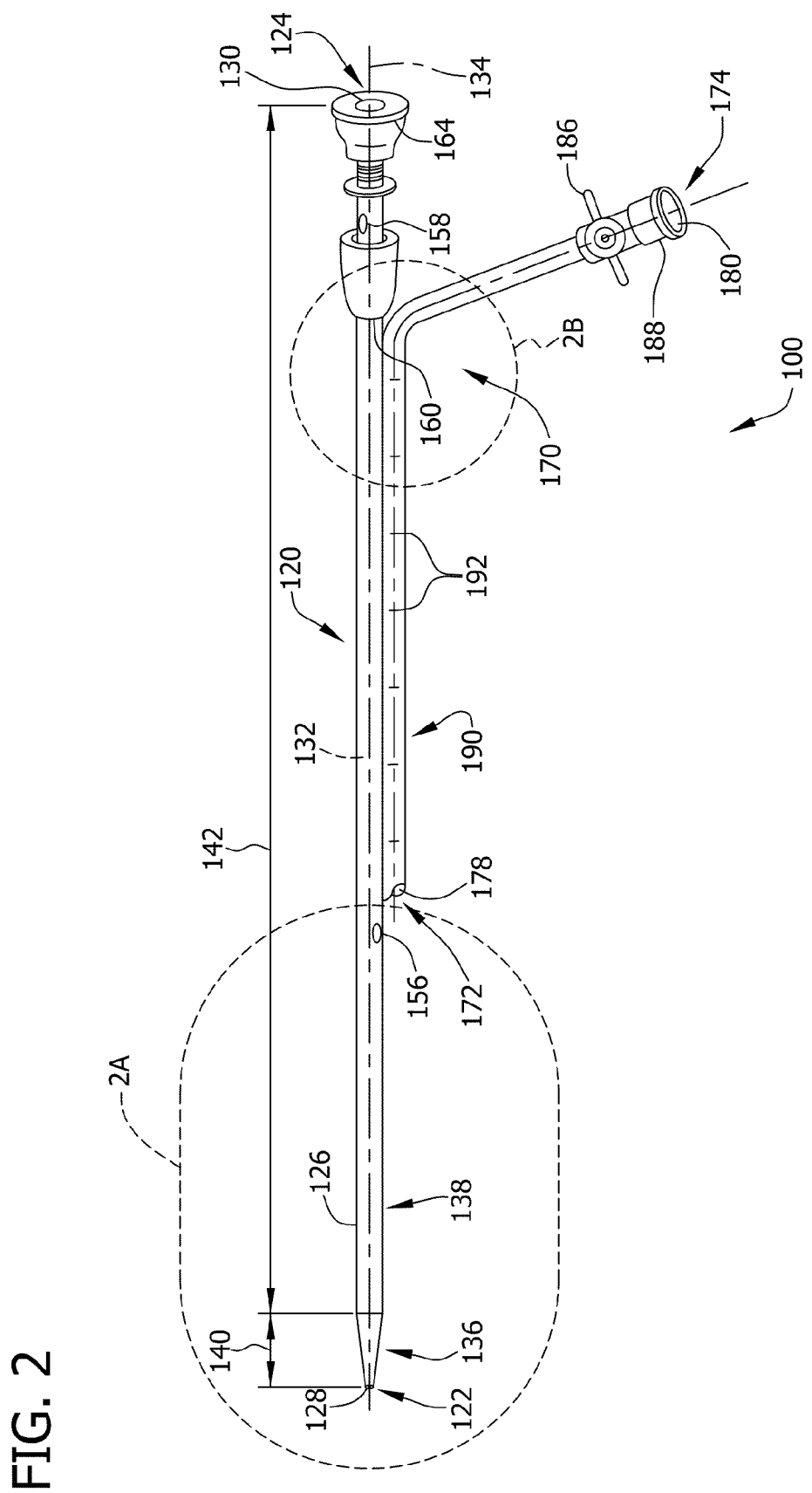
FIG. 2 is a perspective view of the hemostatic device shown in FIG. 1.
Figure 2A:
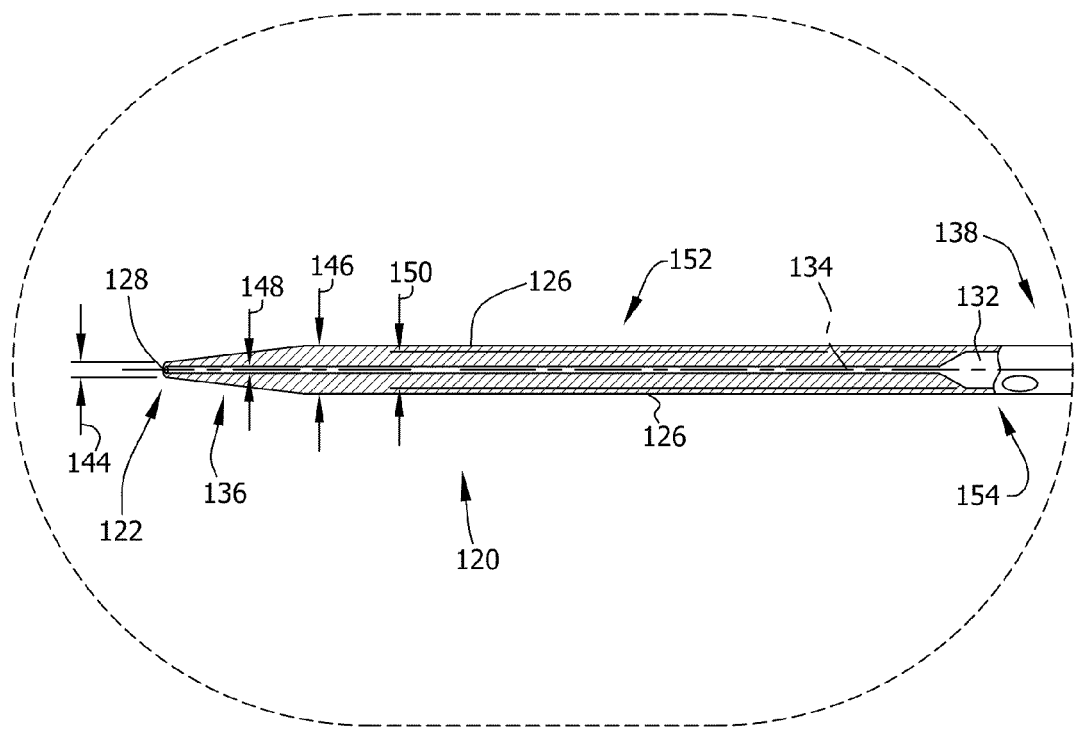
FIGS. 2A and 2B are cut-away views of the hemostatic device shown in FIG. 1.
Figure 2B:
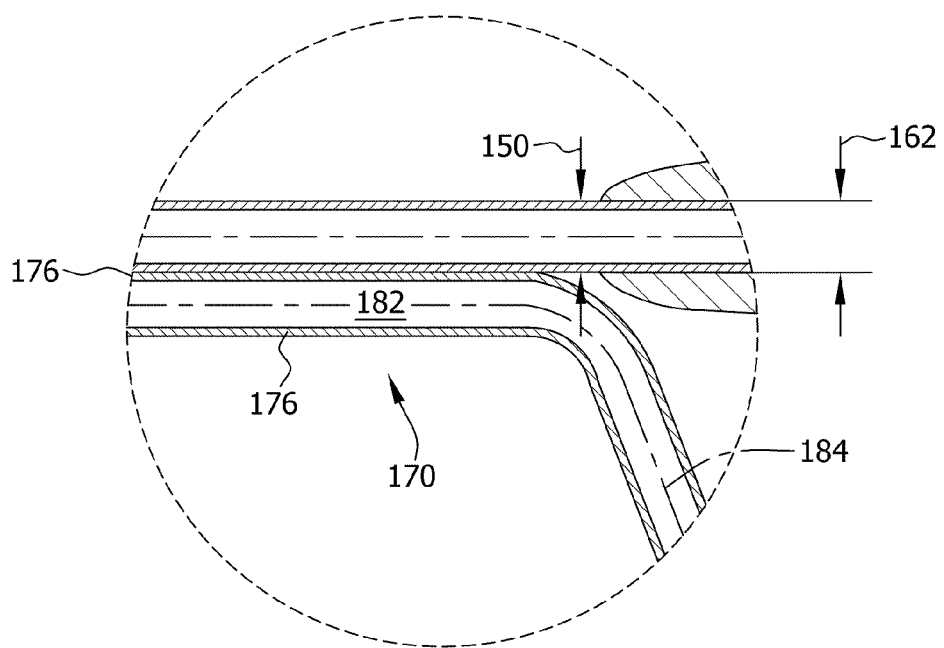

FIG. 1 is a partial cross-sectional view of an access site including an exemplary hemostatic device 100, a guidewire 102, and a vessel or, more particularly, an artery 110 within subcutaneous tissue 112 under a skin surface 114. FIG. 2 is a perspective view of hemostatic device 100, and FIGS. 2A and 2B are detailed cut-away views of hemostatic device 100. In the exemplary embodiment, hemostatic device 100 includes a locator device 120 having a distal end 122 and a proximal end 124. In the exemplary embodiment, locator device 120 extends longitudinally approximately 20.0 centimeters (cm) from distal end 122 to proximal end 124.

In the exemplary embodiment, locator device 120 includes a sidewall 126 having a distal end opening 128, a proximal end opening 130, and a lumen 132 defined therebetween substantially aligned along a center axis 134. In the exemplary embodiment, lumen 132 is configured to channel a first fluid therethrough.

In the exemplary embodiment, locator device 120 includes a first section 136 and a second section 138. First section 136 extends longitudinally a first distance 140 from distal end 122, and second section 138 extends longitudinally a second distance 142 from proximal end 124. First distance 140 is at least approximately 0.5 cm, and second distance 142 is at most approximately 19.5 cm. More particularly, in the exemplary embodiment, first distance 140 is approximately 1.0 cm, and second distance 142 is approximately 19.0 cm.

In the exemplary embodiment, locator device 120 is tapered at distal end 122 to facilitate traversing locator device 120 under skin surface 114 and through subcutaneous tissue 112. First section 136 has a first outer diameter 144, and second section 138 has a second outer diameter 146 that is larger than first outer diameter 144. Second outer diameter 146 is approximately 2 millimeters (mm) or 6 French (Fr). In another embodiment, second outer diameter 146 is approximately 2.67 mm or 8 Fr. In yet another embodiment, second outer diameter 146 is approximately 3.33 mm or 10 Fr.

In the exemplary embodiment, locator device 120 is configured to receive guidewire 102 that extends longitudinally therethrough. More specifically, distal end opening 128, first section 136, second section 138, and proximal end opening 130 are sized such that guidewire 102 is capable of extending longitudinally through lumen 132 between proximal end opening 130 and distal end opening 128. In the exemplary embodiment, guidewire 102 has an outer diameter of approximately 0.035 inches or 0.089 cm.

In the exemplary embodiment, first section 136 has a first inner diameter 148 that is approximately 0.089 cm, and second section 138 has a second inner diameter 150 that is larger than 0.089 cm. More specifically, in the exemplary embodiment, second section 138 has a first subsection 152 that has first inner diameter 148 and a second subsection 154 that has second inner diameter 150. In one embodiment, second inner diameter 150 is approximately 0.059 inches or 0.150 cm. In another embodiment, second inner diameter 150 is approximately 0.087 inches or 0.221 cm. In yet another embodiment, second inner diameter 150 is approximately 0.113 inches or 0.287 cm.

As shown in FIG. 1, sidewall 126 includes a distal opening 156 and a proximal opening 158 extending radially therethrough. Distal opening 156 and proximal opening 158 are in fluid communication with lumen 132. In the exemplary embodiment, distal opening 156 and proximal opening 158 are positioned within second section 138. More specifically, in the exemplary embodiment, first subsection 152 extends longitudinally between first section 136 and distal opening 156, and second subsection extends longitudinally between distal opening 156 and proximal end 124. In the exemplary embodiment, distal opening 156 is positioned approximately 8.0 cm from distal end 122, and proximal opening 158 is positioned approximately 1.0 cm from proximal end 124.

In the exemplary embodiment, locator device 120 includes a first device valve 160 positioned adjacent proximal opening 158. First device valve 160 is actuatable between an open position and a closed position to selectively restrict access to a portion of locator device 120. In the open position, proximal opening 158 is at least partially exposed such that the fluid may flow into and/or out from lumen 132 through proximal opening 158. In contrast, in the closed position, proximal opening 158 is substantially covered by first device valve 160 such that a fluid is restricted from flowing into and/or out from lumen 132 through proximal opening 158. In the exemplary embodiment, first device valve 160 is a sleeve that has an inner diameter 162 that is larger than second outer diameter 146 such that first device valve 160 is slidable about second section 138. In the exemplary embodiment, first device valve 160 extends longitudinally approximately 1.0 cm about locator device 120.

Additionally, in the exemplary embodiment, locator device 120 includes a second device valve 164 positioned adjacent proximal end opening 130. Second device valve 164 is actuatable between an open position and a closed position to selectively restrict access to a portion of locator device 120. In the open position, proximal end opening 130 is at least partially exposed such that guidewire 102 may extend through proximal end opening 130. In contrast, in the closed position, proximal end opening 130 is substantially covered by second device valve 164 such that a fluid is restricted from flowing into and/or out from lumen 132 through proximal end opening 130. In the exemplary embodiment, second device valve 164 is a manual-adjusting valve.

In the exemplary embodiment, hemostatic device 100 further includes an injection tube 170 having a distal end 172 and a proximal end 174. Injection tube 170 extends longitudinally at least 6.0 cm from distal end 172 to proximal end 174. More particularly, injection tube 170 extends longitudinally approximately 8.0 cm from distal end 172 to proximal end 174. Injection tube 170 includes a sidewall 176 having a distal end opening 178, a proximal end opening 180, and a lumen 182 defined therebetween. In the exemplary embodiment, distal end opening 178, proximal end opening 180, and lumen 182 are substantially aligned along a center axis 184, and lumen 182 is configured to channel a second fluid therethrough.

In the exemplary embodiment, injection tube 170 is coupled to locator device 120 such that distal end 172 of injection tube 170 is positionable substantially adjacent artery 110. More specifically, when distal opening 156 of locator device 120 is positioned within artery 110, distal end 172 is positionable substantially adjacent to and outside, artery 110. Distal end 172 of injection tube 170 is positioned approximately 9.0 cm from distal end 122 of locator device 120 such that distal end 172 is positioned approximately 1.0 cm from distal opening 156. In one embodiment, locator device 120 and injection tube 170 are substantially concentric.

In the exemplary embodiment, injection tube 170 includes a tube valve 186 positioned adjacent proximal end opening 180. Tube valve 186 is actuatable between an open position and a closed position to selectively restrict access to a portion of tube valve 186. In the open position, proximal end opening 180 is at least partially exposed such that the fluid may flow into and/or out from lumen 182 through proximal end opening. In contrast, in the closed position, proximal end opening 180 is substantially covered by tube valve 186 such that a fluid is restricted from flowing into and/or out from lumen 182 through proximal end opening 180. In the exemplary embodiment, tube valve 186 is a stop cock and includes a side port 188. In the exemplary embodiment, the fluid may be injected into lumen 182 through side port 188.

Injection tube 170 includes an indicator 190 that indicates a length of locator device 120 and/or injection tube 170. More specifically, indicator 190 provides an indication of how much of injection tube 170 is under skin surface 114. In the exemplary embodiment, indicator 190 includes a plurality of markings 192 that are spaced evenly along injection tube 170. More specifically, in the exemplary embodiment, there is at least one marking 192 for each centimeter of injection tube 170.

FIG. 3 is a flow chart illustrating an exemplary method 200 using hemostatic device 100. During operation, hemostatic device 100 is used for sealing a puncture of artery 110 within subcutaneous tissue 112 under a skin surface 114.

In the exemplary embodiment, a sheath (not shown) used during a medical procedure, such as a cardiac catheterization or a peripheral endovascular procedure, is withdrawn 202 such that a tip of the sheath is positioned approximately 10.0 cm from the access site and the sheath is free of at least some devices. A limited angiography is performed 204 through the sheath to assess the puncture of artery 110 and to ensure that the sheath is positioned within artery 110.

In the exemplary embodiment, guidewire 102 is advanced 206 through the sheath to artery 110 such that a tip of guidewire 102 is positioned at least approximately 5.0 cm beyond the tip of the sheath. More particularly, guidewire 102 is advanced 206 to position the tip of guidewire 102 approximately 10.0 cm beyond the tip of the sheath. Manual pressure is applied 208 over the access site, and the sheath is withdrawn 210 from the access site over guidewire 102. A locator device 120 is determined or selected 212 based on a size of the sheath. For example, in one embodiment, locator device 120 is selected 212 to have an outer diameter that is approximately the same as an outer diameter of the sheath.

In the exemplary embodiment, locator device 120 is advanced 214 into artery 110 until a first fluid is channeled through locator device 120. More specifically, in the exemplary embodiment, locator device 120 is advanced 214 or slid along guidewire 102 under skin surface 114, through subcutaneous tissue 112, and to artery 110 until distal opening 156 is positioned within artery 110 and a fluid such as blood flows into distal opening 156, through lumen 132, and out from proximal opening 158. In the exemplary embodiment, locator device 120 is advanced 214 under skin level for approximately 8.0 cm.

Proximal opening 158 provides a visual cue that distal opening 156 is within artery 110 when the blood flows through proximal opening 158. To reduce an amount of blood that refluxes through proximal opening 158, first device valve 160 is actuated 216 to the closed position to restrict the blood from flowing out from proximal opening 158 and/or through lumen 132. Moreover, guidewire 102 is withdrawn 218 from artery 110 and/or locator device 120, and second device valve 164 is actuated 220 to the closed position to restrict the blood from flowing through proximal end opening 130 and/or through lumen 132.

Distal end 172 of injection tube 170 is positioned 222 substantially adjacent to artery 110. More specifically, the relative positioning of locator device 120 and injection tube 170 enables distal end 172 of injection tube 170 to be positioned 222 substantially adjacent to and just outside artery 110 when distal opening 156 is initially advanced within artery 110.

In the exemplary embodiment, a second fluid or, more particularly, a flowable gelatin is injected 224 around artery 110 and along a tract through subcutaneous tissue 112 between artery 110 and skin surface 114 through injection tube 170 to facilitate sealing the puncture of artery 110. More specifically, in the exemplary embodiment, the flowable gelatin is prepared 226 and received within a syringe (not shown), and the syringe is coupled 228 to side port 188 of injection tube 170.

The flowable gelatin is injected 224 through injection tube 170, side port 188 is rotated 230 approximately 180° about center axis 134, and additional flowable gelatin is injected 232 through injection tube 170. In the exemplary embodiment, the injection process is repeated as hemostatic device 100 is withdrawn 234 from artery 110 a length at a time until hemostatic device 100 is substantially withdrawn from subcutaneous tissue 112. More specifically, hemostatic device 100 is systematically positioned within subcutaneous tissue 112 based on at least one length indicated by indicator 190, and the flowable gelatin is injected 224 through injection tube 170, side port 188 is rotated 230 approximately 180°, and additional flowable gelatin is injected 232 through injection tube 170 for each position. In one embodiment, indicator 190 provides a visual cue that a length of injection tube 170 is under skin surface 114 and facilitates maintaining the length and/or systematically adjusting the length.

In the exemplary embodiment, when distal end 172 of injection tube 170 is substantially adjacent skin surface 114, hemostatic device 100 is withdrawn 234 from artery 110 and/or subcutaneous tissue 112. In the exemplary embodiment, direct, non-occlusive manual pressure is continuously applied 236 to the access site until hemostasis is achieved.

The methods and systems described herein relate to medical devices and, more particularly, to a hemostatic device. The hemostatic device described herein facilitates sealing a puncture of a vessel. More particularly, the hemostatic device enables positioning an injection tube adjacent to the vessel to inject a gelatin through the injection tube. As such, the hemostatic device facilitates reducing a time required for hemostasis and ambulation.

Exemplary embodiments of medical devices are described above in detail. The methods and systems are not limited to the specific embodiments described herein, but rather, operations of the methods and components of the systems may be utilized independently and separately from other operations and/or components described herein. For example, the methods and apparatus described herein may have other industrial and/or consumer applications and are not limited to practice with medical devices as described herein. Rather, one or more embodiments may be implemented and utilized in connection with other industries.

As used herein, an element or step recited in the singular and proceeded with the word "a" or "an" should be understood as not excluding plural said elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A hemostatic device for sealing a puncture of a vessel, said hemostatic device comprising:
   a locator device comprising a sidewall, a distal end opening, a proximal end opening, a first side opening extending through the sidewall, and a device valve slidable along a length of the sidewall, the sidewall defining a lumen extending between the distal end opening and the proximal end opening, the lumen in fluid communication with at least the first side opening and configured to channel a first fluid flow through the first side opening, into the lumen, and to the proximal opening, the device valve actuatable to selectively control the first fluid flow through the lumen; and
   an injection tube coupled to the locator device such that a distal end of the injection tube is positionable substantially adjacent to and outside the vessel when the first side opening of the locator device is positioned within the vessel, the injection tube configured to channel a second fluid flow therethrough.

2. A hemostatic device in accordance with claim 1, wherein the sidewall includes a first section having a first inner diameter and a second section having a second inner diameter that is greater than the first inner diameter.

3. A hemostatic device in accordance with claim 1, wherein the sidewall has an inner diameter that is sized to receive a guidewire.

4. A hemostatic device in accordance with claim 1, wherein the sidewall includes a first section having an outer diameter that tapers toward a distal end of the locator device and a second section having an outer diameter that is substantially uniform such that the outer diameter of the first portion is the same as or less than the outer diameter of the second portion.

5. A hemostatic device in accordance with claim 1, wherein the locator device further comprises a second device valve that is actuatable to selectively control the first fluid flow through the lumen.

6. A hemostatic device in accordance with claim 1, wherein the injection tube further comprises a tube valve that is actuatable to selectively control a second fluid flow through the injection tube.

7. A hemostatic device in accordance with claim 1, wherein at least one of the locator device and the injection tube further comprises an indicator that indicates a length of at least one of the locator device and the injection tube.

8. A hemostatic device for sealing a puncture of a vessel, said hemostatic device comprising:

a locator device comprising a sidewall, a distal end opening, a proximal end opening, a first side opening extending through a distal portion of the sidewall, and a device valve that is actuatable to selectively restrict a first fluid access to a portion of the locator device, the locator device defining a lumen extending between the distal end opening and the proximal end opening, the locator device configured to receive a guidewire through the distal end opening, the lumen, and the proximal end opening, the lumen in fluid communication with at least the first side opening and further configured to channel the first fluid therethrough; and an injection tube coupled to the locator device such that a distal end of the injection tube is positionable substantially adjacent to and outside the vessel when the first side opening of the locator device is positioned within the vessel, the injection tube configured to channel a second fluid therethrough, wherein the locator device includes a second side opening extending through a proximal portion of the sidewall, the lumen in fluid communication with the second side opening, and the device valve actuatable to selectively control the first fluid flow through the first side opening, the lumen and the second side opening.

9. A hemostatic device as recited in claim 8, wherein the second side opening is adjacent the proximal end opening.

10. A hemostatic device for sealing a puncture of a vessel, said hemostatic device comprising:

a locator device comprising a device sidewall and a device valve slidable along a length of the device sidewall, the device sidewall defining a device lumen that is configured to channel a first fluid flow, the locator device includes a distal end opening, a proximal end opening, and a first side opening extending through the sidewall, the device lumen in fluid communication with the distal end opening, the proximal end opening, and the first side opening, the device valve actuatable to selectively control the first fluid flow through the device lumen; and an injection tube coupled to the locator device such that a distal end of the injection tube is positionable substantially adjacent to and outside the vessel when the first side opening of the locator device is positioned within the vessel, the injection tube comprising a tube sidewall that defines a tube lumen configured to channel a second fluid flow therethrough.

11. A hemostatic device in accordance with claim 10, wherein the device sidewall comprises a first section having a first inner diameter and a second section having a second inner diameter that is greater than the first inner diameter.

12. A hemostatic device in accordance with claim 10, wherein the device sidewall has an inner diameter that is sized to receive a guidewire.

13. A hemostatic device in accordance with claim 10, wherein the device sidewall includes a first section having an outer diameter that tapers toward a distal end of the locator device and a second section having an outer diameter that is substantially uniform such that the outer diameter of the first portion is the same or less than the outer diameter of the second portion.

14. A hemostatic device in accordance with claim 10, wherein the locator device further comprises a second device valve that is actuatable to control the first fluid flow through the device lumen.

15. A hemostatic device in accordance with claim 10, wherein the injection tube further comprises a tube valve that is actuatable to selectively control a second fluid flow through the tube lumen.

16. A hemostatic device in accordance with claim 10, wherein at least one of the locator device and the injection tube further comprises an indicator that indicates a length of at least one of the locator device and the injection tube.

17. A hemostatic device for sealing a puncture of a vessel, said hemostatic device comprising:

a locator device comprising a device sidewall and a device valve, the device sidewall defining a device lumen that is configured to channel a first fluid therethrough, the locator device includes a distal end opening, a proximal end opening, and a first side opening extending through a distal portion of the sidewall, the device lumen in fluid communication with the distal end opening, the proximal end opening, and the first side opening, the locator device configured to receive a guidewire through the distal end opening, the device lumen, and the proximal end opening, the device valve actuatable to selectively restrict the first fluid access to the device lumen; and an injection tube coupled to the locator device such that a distal end of the injection tube is positionable substantially adjacent to and outside the vessel when the first side opening of the locator device is positioned within the vessel, the injection tube comprising a tube sidewall that defines a tube lumen configured to channel a second fluid therethrough, wherein the locator device includes a second side opening extending through a proximal portion of the sidewall, the lumen in fluid communication with the second side opening, and the device valve actuatable to selectively control the first fluid flow through the first side opening, the lumen and the second side opening.

18. A hemostatic device as recited in claim 17, wherein the second side opening is adjacent the proximal end opening.

* * * * *